United States Patent
Crooks et al.

(10) Patent No.: US 8,653,275 B2
(45) Date of Patent: Feb. 18, 2014

(54) BIS-QUATERNARY AMMONIUM CYCLOPHANE COMPOUNDS THAT INTERACT WITH NEURONAL NICOTINIC ACETYLCHOLINE RECEPTORS

(75) Inventors: Peter Crooks, Nicholasville, KY (US); Linda P. Dwoskin, Lexington, KY (US); Guangrong Zheng, Lexington, KY (US); Sangeetha Sumithran, Lexington, KY (US); Davis D. Allen, Rootstown, OH (US); Zhenfa Zheng, Lexington, KY (US); Paul Lockman, Amarillo, TX (US)

(73) Assignee: University of Kentucky Research Foundation, Lexington, KY (US)

( * ) Notice: Subject to any disclaimer, the term of this patent is extended or adjusted under 35 U.S.C. 154(b) by 853 days.

(21) Appl. No.: 12/300,197

(22) PCT Filed: May 11, 2007

(86) PCT No.: PCT/US2007/011269
§ 371 (c)(1),
(2), (4) Date: May 18, 2010

(87) PCT Pub. No.: WO2007/133614
PCT Pub. Date: Nov. 22, 2007

(65) Prior Publication Data
US 2010/0222377 A1    Sep. 2, 2010

Related U.S. Application Data

(60) Provisional application No. 60/799,881, filed on May 12, 2006.

(51) Int. Cl.
*C07D 211/68* (2006.01)
*A61K 31/435* (2006.01)

(52) U.S. Cl.
USPC .......................................... 546/285; 514/290

(58) Field of Classification Search
USPC .......................................... 546/285; 514/290
See application file for complete search history.

(56) References Cited

U.S. PATENT DOCUMENTS

| | | | |
|---|---|---|---|
| 6,376,510 | B1 | 4/2002 | Gyermek et al. |
| 2003/0027810 | A1 | 2/2003 | Efange et al. |
| 2005/0080078 | A1 | 4/2005 | Aquila et al. |
| 2005/0107399 | A1 | 5/2005 | Bowman et al. |
| 2005/0261334 | A1 | 11/2005 | Crooks et al. |

OTHER PUBLICATIONS

Wanner et al. (European Journal of Organic Chemistry (1998), (5), 889-895).*
Zheng et al. (Bioorganic & Medicinal Chemistry 14 (2006) 3017-3037).*
Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chapters 9-10 provided.*

* cited by examiner

*Primary Examiner* — Robert Havlin
(74) *Attorney, Agent, or Firm* — Crowell & Moring LLP

(57) ABSTRACT

Provided are bis-quaternary ammonium cyclophane compounds which are modulators of nicotinic acetylcholine receptors. Also provided are methods of using the compounds for modulating the function of a nicotinic acetylcholine receptor, and for the prevention and/or treatment of central nervous system disorders, substance use and/or abuse, and or gastrointestinal tract disorders.

9 Claims, No Drawings

BIS-QUATERNARY AMMONIUM CYCLOPHANE COMPOUNDS THAT INTERACT WITH NEURONAL NICOTINIC ACETYLCHOLINE RECEPTORS

CONTINUING APPLICATION DATA

This application is a national stage of PCT/US2007/011269, filed May 11, 2007, which claims benefit of U.S. Provisional Application No. 60/799,881, filed May 12, 2006, which is incorporated herein by reference in its entirety.

IDENTIFICATION OF FEDERAL FUNDING

The present invention was supported by Grant NIH U19DA017548 from the National Institutes of Health, and therefore the government may have rights in the invention.

FIELD OF THE INVENTION

The invention relates to bis-quaternary ammonium cyclophane compounds that interact with neuronal nicotinic receptors, and to methods of using the compounds to treat central nervous system diseases and pathologies.

BACKGROUND OF THE INVENTION

S(−)-Nicotine (NIC) activates presynaptic and postsynaptic neuronal nicotinic receptors that evoke the release of neurotransmitters from presynaptic terminals and that modulate the depolarization state of the postsynaptic neuronal membrane, respectively. Thus, nicotine produces its effect by binding to a family of ligand-gated ion channels, stimulated by acetylcholine (ACh) or nicotine which causes the ion channel to open and cations to flux with a resulting rapid (millisecond) depolarization of the target cell.

Neuronal nicotinic receptors are composed of two types of subunits, α and β, and assemble as heteromeric receptors with the general stoichiometry of 2α and 3β or as homomeric receptors with 5α subunits. Nine subtypes of the α subunit (α2 to α10) and three subtypes of the β unit (β2 to β4) are found in the central nervous system. The most common nicotinic receptor subtype in the brain is composed of two α4 and three β2 subunits, i.e., α4β2. These subunits display different, but overlapping, patterns of expression in the brain. Examples of heteromeric receptor subtypes include α4β2, α3β2, α3β4, α6β2, α6β2β3, α4α5β2, α6α5β2, α6α4β2, α6α4β2β3, α4β2β4, α3β2β4, and others. The predominant homomeric subtype includes α7, but other combinations have also been proposed.

For the most part, the actual subunit compositions and stoichiometries of nicotinic receptors in the brain remain to be elucidated. Thus, neuronal nicotinic receptor subtype diversity originates from differences in the amino acid sequence at the subunit level and from the multiple combinations of assemblies of subunits into functional receptor proteins, which affords a wide diversity of pharmacological specificity.

In spite of the extensive diversity in neuronal nicotinic receptor messenger RNA expression, only a limited number of tools are available to study the pharmacology of native receptors. Radioligands are used in many studies. [$^3$H]NIC appears to label the same sites in the brain as [$^3$H]ACh. It has been estimated that over 90% of [$^3$H]NIC binding in the brain is due to association with the heteromeric receptor that is composed of α4 and β2 subunits. Also abundant in the central nervous system are the homomeric receptors labeled by [$^3$H] methyllycaconitine (MLA), which has high affinity for the α7 nicotinic receptor subtype. Nicotinic receptor subtypes can be studied using functional assays, such as NIC-evoked neurotransmitter release (e.g., [$^3$H]dopamine (DA) release, [$^3$H]norepinephrine (NE) release, [$^3$H]serotonin (5-HT) release, [$^3$H]gamma-aminobutyric acid (GABA) release and [$^3$H]glutamate release) from superfused rat brain slices. Nicotinic receptors are located in the cell body and terminal areas of these neurotransmitter systems. NIC facilitates neurotransmitter release from nerve terminals.

The structural and functional diversity of central nervous system nicotinic receptors has stimulated a great deal of interest in developing novel, subtype-selective agonists and/or antagonists. Some of these agonists are currently being evaluated in clinical trials for cognitive enhancement and neuroprotective effects, potentially beneficial for disease states such as Alzheimer's and Parkinson's disease, as well as for treatment of drug abuse, depression, obesity and pain relief.

SUMMARY OF THE INVENTION

In one embodiment, compounds corresponding to the following structure are provided.

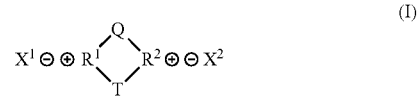

(I)

$X^{1\ominus}$ and $X^{2\ominus}$ are each independently an organic or inorganic anion.

Q and T are each independently attached to $R^1$ and $R^2$. Q and T are each independently selected from alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic; $SOY^1$, $SO_2Y^1$, $SO_2OY^1$ or $SO_2NHY^1$, where $Y^1$ is selected from hydrogen, lower alkyl, alkenyl, alkynyl or aryl, and where $Y^1$ is not hydrogen in $SOY^1$ and if $Y^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, aryloxy, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$, where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur.

$R^1$ and $R^2$ are each independently five or six membered rings as shown in formulas (IIA) and (IIB), wherein each ring of $R^1$ and $R^2$ has one, two or three nitrogen atoms, each ring of $R^1$ and $R^2$ has one quaternized nitrogen, and two of $R^3$ through $R^{24}$ of each $R^1$ and two of $R^3$ through $R^{24}$ of each $R^2$ are replaced by one attachment to Q and one attachment to T.

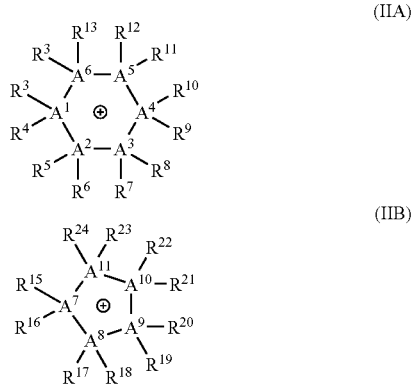

$A^1$ is carbon or nitrogen, provided that when $A^1$ joins a ring atom with an unsaturated bond or is a nitrogen, $R^3$ is absent, and when $A^1$ joins a ring atom with an unsaturated bond and is a nitrogen, both $R^3$ and $R^4$ are absent.

$A^2$ is carbon or nitrogen, provided that when $A^2$ joins a ring atom with an unsaturated bond or is a nitrogen, $R^5$ is absent, and when $A^2$ joins a ring atom with an unsaturated bond and is a nitrogen, both $R^5$ and $R^6$ are absent.

$A^3$ is carbon or nitrogen, provided that when $A^3$ joins a ring atom with an unsaturated bond or is a nitrogen, $R^7$ is absent, and when $A^3$ joins a ring atom with an unsaturated bond and is a nitrogen, both $R^7$ and $R^8$ are absent.

$A^4$ is carbon or nitrogen, provided that when $A^4$ joins a ring atom with an unsaturated bond or is a nitrogen, $R^9$ is absent, and when $A^4$ joins a ring atom with an unsaturated bond and is a nitrogen, both $R^9$ and $R^{10}$ are absent.

$A^5$ is carbon or nitrogen, provided that when $A^5$ joins a ring atom with an unsaturated bond or is a nitrogen, $R^{11}$ is absent, and when $A^5$ joins a ring atom with an unsaturated bond and is a nitrogen, both $R^{11}$ and $R^{12}$ are absent.

$A^6$ is carbon or nitrogen, provided that when $A^6$ joins a ring atom with an unsaturated bond or is a nitrogen, $R^{13}$ is absent, and when $A^6$ joins a ring atom with an unsaturated bond and is a nitrogen, both $R^{13}$ and $R^{14}$ are absent.

$A^7$ is carbon or nitrogen, provided that when $A^7$ joins a ring atom with an unsaturated bond or is a nitrogen, $R^{15}$ is absent, and when $A^7$ joins a ring atom with an unsaturated bond and is a nitrogen, both $R^{15}$ and $R^{16}$ are absent.

$A^8$ is carbon or nitrogen, provided that when $A^8$ joins a ring atom with an unsaturated bond or is a nitrogen, $R^{17}$ is absent, and when $A^8$ joins a ring atom with an unsaturated bond and is a nitrogen, both $R^{17}$ and $R^{18}$ are absent.

$A^9$ is carbon or nitrogen, provided that when $A^9$ joins a ring atom with an unsaturated bond or is a nitrogen, $R^{19}$ is absent, and when $A^9$ joins a ring atom with an unsaturated bond and is a nitrogen, both $R^{19}$ and $R^{20}$ are absent.

$A^{10}$ is carbon or nitrogen, provided that when $A^{10}$ joins a ring atom with an unsaturated bond or is a nitrogen, $R^{21}$ is absent, and when $A^{10}$ joins a ring atom with an unsaturated bond and is a nitrogen, both $R^{21}$ and $R^{22}$ are absent.

$A^{11}$ is carbon or nitrogen, provided that when $A^{11}$ joins a ring atom with an unsaturated bond or is a nitrogen, $R^{23}$ is absent, and when $A^{11}$ joins a ring atom with an unsaturated bond and is a nitrogen, both $R^{23}$ and $R^{24}$ are absent.

$R^3$, $R^4$, $R^5$, $R^6$, $R^7$, $R^8$, $R^9$, $R^{10}$, $R^{11}$, $R^{12}$, $R^{13}$ and $R^{14}$, or $R^{15}$, $R^{16}$, $R^{17}$, $R^{18}$, $R^{19}$, $R^{20}$, $R^{21}$, $R^{22}$, $R^{23}$ and $R^{24}$, when present, are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, halo, cyano, nitro; or two adjacent groups $R^3$ through $R^{14}$, or groups $R^{15}$ through $R^{24}$, together with the atoms to which they are attached on the ring of (IIA) or (IIB) independently form a three to eight member cyclolkane, substituted cycloalkane, cycloalkene, substituted cycloalkene, aryl, substituted aryl, heterocycle with one to three hetero atoms of nitrogen, oxygen or sulfur in the ring, or substituted heterocycle with one to three hetero atoms of nitrogen, oxygen or sulfur in the ring; and when all of the bonds to the ring ammonium nitrogen are saturated, then any of $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ or $R^{24}$ which is attached to the ammonium nitrogen is a straight or branched alkyl group of four carbons or fewer.

In another embodiment, a composition is provided comprising a pharmaceutically acceptable carrier and a compound as described above.

In another embodiment, a method is provided for selectively modulating the function of a nicotinic acetylcholine receptor comprising administering a therapeutically effective amount of a compound as described above to a mammalian subject in need thereof.

In another embodiment, a method is provided for facilitating transport of a compound of the invention into the central nervous system by interaction of the compound with the blood brain barrier choline transporter.

In another embodiment, a method is provided for preventing and/or treating a central nervous system associated disorder, for example, schizophrenia, Tourettes', Huntington's Chorea, Parkinson's disease, Alzheimer's disease, and related conditions, comprising administering a therapeutically effective amount of a compound as described above to a mammalian subject in need thereof.

In another embodiment, a method is provided for preventing and/or treating substance use and/or abuse comprising administering a therapeutically effective amount of a compound as described above to a mammalian subject in need thereof.

In another embodiment, a method is provided for preventing and/or treating gastrointestinal tract disorders comprising administering a therapeutically effective amount of a compound as described above to a mammalian subject in need thereof.

Other methods, features and advantages of the present invention will be or become apparent to one with skill in the art upon examination of the following detailed descriptions. It is intended that all such additional methods, features and advantages be included within this description, be within the scope of the present invention, and be protected by the accompanying claims.

DETAILED DESCRIPTION OF THE INVENTION

Before the present compositions and methods are described, it is to be understood that the invention is not limited to the particular methodologies, protocols, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The term "nicotinic acetylcholine receptor" refers to the endogenous acetylcholine receptor having binding sites for acetylcholine which also bind to nicotine. The term "nicotinic acetylcholine receptor" includes the term "neuronal nicotinic acetylcholine receptor."

The terms "subtype of nicotinic acetylcholine receptor," and "nicotinic acetylcholine receptor subtype" refer to various subunit combinations of the nicotinic acetylcholine receptor, and may refer to a particular homomeric or heteromeric complex, or multiple homomeric or heteromeric complexes.

The term "choline transporter" refers to the endogenous choline transporter having binding sites for choline which also bind to positively charged quaternary ammonium groups. The term "choline transporter" includes the term "blood brain barrier choline transporter."

The term "agonist" refers to a substance which interacts with a receptor and increases or prolongs a physiological response (i.e. activates the receptor).

The term "partial agonist" refers to a substance which interacts with and activates a receptor to a lesser degree than an agonist.

The term "antagonist" refers to a substance which interacts with and decreases the extent or duration of a physiological response of that receptor.

The terms "disorder," "disease," and "condition" are used inclusively and refer to any status deviating from normal.

The term "central nervous system associated disorders" includes any cognitive, neurological, and mental disorders causing aberrant or pathological neural signal transmission, such as disorders associated with the alteration of normal neurotransmitter release in the brain.

The term "lower alkyl" refers to straight or branched chain alkyl radicals having in the range of 1 to 4 carbon atoms.

The term "alkyl" refers to straight or branched chain alkyl radicals having 1 to 19 carbon atoms, and "substituted alkyl" refers to alkyl radicals further bearing one or more substituents including, but not limited to, hydroxy, alkoxy (of a lower alkyl group), mercapto (of a lower alkyl group), aryl, heterocyclic, halogen, trifluoromethyl, cyano, nitro, amino, carboxyl, carbamate, sulfonyl, and sulfonamide.

The term "cycloalkyl" refers to cyclic ring-containing moieties containing 3 to 8 carbon atoms, and "substituted cycloalkyl" refers to cycloalkyl moieties further bearing one or more substituents as set forth above.

The term "alkenyl" refers to straight or branched chain hydrocarbyl groups having at least one carbon-carbon double bond and having 2 to 19 carbon atoms, and "substituted alkenyl" refers to alkenyl groups further bearing one or more substituents as set forth above.

The term "alkynyl" refers to straight or branched chain hydrocarbyl moieties having at least one carbon-carbon triple bond and having 2 to 19 carbon atoms, and "substituted alkynyl" refers to alkynyl moieties further bearing one or more substituents as set forth above.

The term "aryl" refers to aromatic groups having 6 to 24 carbon atoms, and "substituted aryl" refers to aryl groups further bearing one or more substituents as set forth above.

The term "alkylaryl" refers to alkyl-substituted aryl groups, and "substituted alkylaryl" refers to alkylaryl groups further bearing one or more substituents as set forth above.

The term "arylalkyl" refers to aryl-substituted alkyl groups, and "substituted arylalkyl" refers to arylalkyl groups further bearing one or more substituents as set forth above.

The term "arylalkenyl" refers to aryl-substituted alkenyl groups, and "substituted arylalkenyl" refers to arylalkenyl groups further bearing one or more substituents as set forth above.

The term "arylalkynyl" refers to aryl-substituted alkynyl groups, and "substituted arylalkynyl" refers to arylalkynyl groups further bearing one or more substituents as set forth above.

The term "heterocyclic" refers to cyclic moieties containing one or more heteroatoms as part of the ring structure and having 3 to 24 carbon atoms, and "substituted heterocyclic" refers to heterocyclic moieties further bearing one or more substituents as set forth above.

The term "acyl" refers to alkyl-carbonyl groups, and "substituted acyl" refers to acyl groups further bearing one or more substituents as set forth above.

The term "halogen" refers to fluoride, chloride, bromide or iodide groups.

It is understood that in all substituted groups defined above, polymers arrived at by defining substituents with further substituents to themselves (e.g. substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Compounds of the present invention are bis-quaternary ammonium cyclophane compounds corresponding to Formula (I):

$X^{1\ominus}$ and $X^{2\ominus}$ are each independently an organic or inorganic anion.

Q and T are each independently attached to $R^1$ and $R^2$. Q and T are each independently selected from alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic; $SOY^1$, $SO_2Y^1$, $SO_2OY^1$ or $SO_2NHY^1$, where $Y^1$ is selected from hydrogen, lower alkyl, alkenyl, alkynyl or aryl, and where $Y^1$ is not hydrogen in $SOY^1$ and if $Y^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, aryloxy, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$, where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur.

$R^1$ and $R^2$ are each independently five or six membered rings as shown in formulas (IIA) and (IIB), wherein each ring of $R^1$ and $R^2$ has one, two or three nitrogen atoms, each ring of $R^1$ and $R^2$ has one quaternized nitrogen, and two of $R^3$ through $R^{24}$ of each $R^1$ and two of $R^3$ through $R^{24}$ of each $R^2$ are replaced by one attachment to Q and one attachment to T.

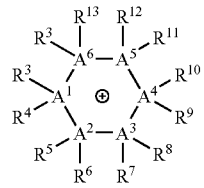
(IIA)

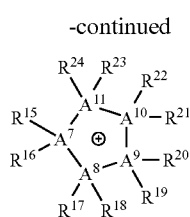
(IIB)

$A^1$ is carbon or nitrogen, provided that when $A^1$ joins a ring atom with an unsaturated bond or is a nitrogen, $R^3$ is absent, and when $A^1$ joins a ring atom with an unsaturated bond and is a nitrogen, both $R^3$ and $R^4$ are absent.

$A^2$ is carbon or nitrogen, provided that when $A^2$ joins a ring atom with an unsaturated bond or is a nitrogen, $R^5$ is absent, and when $A^2$ joins a ring atom with an unsaturated bond and is a nitrogen, both $R^5$ and $R^6$ are absent.

$A^3$ is carbon or nitrogen, provided that when $A^3$ joins a ring atom with an unsaturated bond or is a nitrogen, $R^7$ is absent, and when $A^3$ joins a ring atom with an unsaturated bond and is a nitrogen, both $R^7$ and $R^8$ are absent.

$A^4$ is carbon or nitrogen, provided that when $A^4$ joins a ring atom with an unsaturated bond or is a nitrogen, $R^9$ is absent, and when $A^4$ joins a ring atom with an unsaturated bond and is a nitrogen, both $R^9$ and $R^{10}$ are absent.

$A^5$ is carbon or nitrogen, provided that when $A^5$ joins a ring atom with an unsaturated bond or is a nitrogen, $R^{11}$ is absent, and when $A^5$ joins a ring atom with an unsaturated bond and is a nitrogen, both $R^{11}$ and $R^{12}$ are absent.

$A^6$ is carbon or nitrogen, provided that when $A^6$ joins a ring atom with an unsaturated bond or is a nitrogen, $R^{13}$ is absent, and when $A^6$ joins a ring atom with an unsaturated bond and is a nitrogen, both $R^{13}$ and $R^{14}$ are absent.

$A^7$ is carbon or nitrogen, provided that when $A^7$ joins a ring atom with an unsaturated bond or is a nitrogen, $R^{15}$ is absent, and when $A^7$ joins a ring atom with an unsaturated bond and is a nitrogen, both $R^{15}$ and $R^{16}$ are absent.

$A^8$ is carbon or nitrogen, provided that when $A^8$ joins a ring atom with an unsaturated bond or is a nitrogen, $R^{17}$ is absent, and when $A^8$ joins a ring atom with an unsaturated bond and is a nitrogen, both $R^{17}$ and $R^{18}$ are absent.

$A^9$ is carbon or nitrogen, provided that when $A^9$ joins a ring atom with an unsaturated bond or is a nitrogen, $R^{19}$ is absent, and when $A^9$ joins a ring atom with an unsaturated bond and is a nitrogen, both $R^{19}$ and $R^{20}$ are absent.

$A^{10}$ is carbon or nitrogen, provided that when $A^{10}$ joins a ring atom with an unsaturated bond or is a nitrogen, $R^{21}$ is absent, and when $A^{10}$ joins a ring atom with an unsaturated bond and is a nitrogen, both $R^{21}$ and $R^{22}$ are absent.

$A^{11}$ is carbon or nitrogen, provided that when $A^{11}$ joins a ring atom with an unsaturated bond or is a nitrogen, $R^{23}$ is absent, and when $A^{11}$ joins a ring atom with an unsaturated bond and is a nitrogen, both $R^{23}$ and $R^{24}$ are absent.

$R^3$, $R^4$, $R^5$, $R^6$, $R^7$, $R^8$, $R^9$, $R^{10}$, $R^{11}$, $R^{12}$, $R^{13}$ and $R^{14}$, or $R^{15}$, $R^{16}$, $R^{17}$, $R^{18}$, $R^{19}$, $R^{20}$, $R^{21}$, $R^{22}$, $R^{23}$ and $R^{24}$, when present, are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, halo, cyano, nitro; or two adjacent groups $R^3$ through $R^{14}$, or groups $R^{15}$ through $R^{24}$, together with the atoms to which they are attached on the ring of (IIA) or (IIB) independently form a three to eight member cyclolkane, substituted cycloalkane, cycloalkene, substituted cycloalkene, aryl, substituted aryl, heterocycle with one to three hetero atoms of nitrogen, oxygen or sulfur in the ring, or substituted heterocycle with one to three hetero atoms of nitrogen, oxygen or sulfur in the ring; and when all of the bonds to the ring ammonium nitrogen are saturated, then any of $R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}$ or $R^{24}$ which is attached to the ammonium nitrogen is a straight or branched alkyl group of four carbons or fewer.

For example, $R^1$ and $R^2$ include pyrrole, pyrrolidine, pyrazole, imidazole, 1,2,3-triazole, 1,2,4-triazole, pyridine, pyrimidine, piperidine, quinoline, tetrahydroquinoline, isoquinoline, tetrahydroisoquinoline, pyrazine, piperazine, pyridazine and triazine.

As another example, $R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}$ and $R^{24}$, include hydrogen, methyl, ethyl, propyl, butyl, hydroxymethyl, hydroxyethyl, hydroxypropyl, trifluoromethyl, chloro, bromo, phenyl, pyrrolidine, N-alkyl pyrrolidine (for example where the alkyl chain is methyl, ethyl or propyl), unsaturated pyrrolidine, unsaturated N-alkyl pyrrolidine (for example where the alkyl chain is methyl, ethyl or propyl), aziridine, N-methyl aziridine, azetidine, N-methyl azetidine, unsaturated azetidine, unsaturated N-methyl azetidine, piperidine, N-methyl piperidine, unsaturated piperidine, unsaturated N-methyl piperidine, azepane, N-methyl azepane, unsaturated azepane, unsaturated N-methyl azepane, azocane, N-methyl azocane, unsaturated azocane, unsaturated N-methyl azocane, 1-aza-bicyclo[3.2.1]octane, 1-aza-bicyclo[2.2.1]heptane, 8-methyl-8-aza-bicyclo[3.2.1]octane, 1-aza-tricyclo[3.3.1.1$^{3,7}$]decane, methyl cycloalkyl, methyl substituted cycloalkyl, methylpyrrolidine, methyl N-alkyl pyrrolidine (for example where the alkyl chain is methyl, ethyl or propyl), methyl unsaturated pyrrolidine, methyl unsaturated N-alkyl pyrrolidine (for example where the alkyl chain is methyl, ethyl or propyl), methyl aziridine, methyl N-methyl aziridine, methyl azetidine, methyl N-methyl azetidine, methyl unsaturated azetidine, methyl unsaturated N-methyl azetidine, methyl piperidine, methyl N-methyl piperidine, methyl unsaturated piperidine, methyl unsaturated N-methyl piperidine, methyl azepane, methyl N-methyl azepane, methyl unsaturated azepane, methyl unsaturated N-methyl azepane, methyl azocane, methyl N-methyl azocane, methyl unsaturated azocane, methyl unsaturated N-methyl azocane, methyl-1-aza-bicyclo[3.2.1]octane, methyl-1-aza-bicyclo[2.2.1]heptane, 8-methyl-8-aza-bicyclo[3.2.1] octane, and methyl-1-aza-tricyclo[3.3.1.1$^{3,7}$]decane.

As a further example, when two adjacent groups $R^3$ through $R^{14}$, or groups $R^{15}$ through $R^{24}$, together with the atoms to which they are attached on the ring of (IIA) or (IIB) independently form a three to eight member cyclolkane, substituted cycloalkane, cycloalkene, substituted cycloalkene, aryl, substituted aryl, heterocycle with one to three hetero atoms of nitrogen, oxygen or sulfur in the ring, or substituted heterocycle with one to three hetero atoms of nitrogen, oxygen or sulfur in the ring. For example, possible rings include benzene, pyridine, pyran, indene, isoindene, benzofuran, isobenzofuran, benzo[b]thiophene, benzo[c]thiophene, indole, indolenine, isoindole, cyclopental[b]pyridine, pyrano [3,4-b]pynrole, indazole, indoxazine, benzoxazole, anthranil, naphthalene, tetralin, decalin, chromene, coumarin, chroman-4-one, isocoumarin, isochromen-3-one, quinoline, isoquinoline, cinnoline, quinazoline, naphthyrdine, pyrido[3,4-b]-pyridine, pyridol[3,2-b]pyridine, pyrido[4,3,-b]-pyridine, benzoxazine, anthracene, phenanthrene, phenalene, fluorene, carazole, xanthene, acnidine, octahydro-[1]pyridine, 1-methylocthyloctahydro-[1]pyridine, octahydroindole, 1-methyloctahydro-indole, octahydro-cyclopenta[b]pyrrole, 1-methyloctahydro-cyclopenta[b]pyrrole, decahydroquinoline, and 1-methyldecahydroquinoline.

$X^{1\ominus}$ and $X^{2\ominus}$, for example, include F$^-$, Cl$^-$, Br$^-$, I$^-$, NO$_2^-$, HSO$_4^-$, SO$_4^-$, HPO$_4^-$, PO$_4^{2-}$, methanesulfonate, trifluoromethane sulfate, p-toluenesulfonate, benzenesulfonate, salicylate, proprionate, ascorbate, aspartate, fumarate, galactarate, maleate, citrate, glutamate, glycolate, lactate, malate, maleate, tartrate, oxalate, succinate, or similar pharmaceutically acceptable organic acid addition salts, including the pharmaceutically acceptable salts listed in the Journal of Pharmaceutical Sciences volume 66, page 2, 1977, which are hereby incorporated by reference. The above salt forms may be in some cases hydrates or solvates with alcohols and other solvents.

In a compound of Formula (I), preferably $R^1$ and $R^2$ are six-membered, aromatic rings. More preferably, $R^1$ and $R^2$ are pyridinium rings, such as 1,3-substituted pyridinium rings.

In a compound of Formula (I), preferably $R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}$ or $R^{24}$ is absent or is hydrogen.

In a compound of Formula (I), preferably Q is attached to the nitrogen of a pyridinium ring of $R^1$ and $R^2$. In other preferred embodiments, Q is attached to the nitrogen of a pyridinium ring of $R^1$ and a carbon at the 3-position of a pyridinium ring of $R^2$. Preferably, Q is an alkyl group; more preferably, Q is selected from —(CH$_2$)$_4$—, —(CH$_2$)$_6$—, —(CH$_2$)$_8$—, —(CH$_2$)$_9$—, —(CH$_2$)$_{10}$—, —(CH$_2$)$_{11}$—, and —(CH$_2$)$_{12}$—.

In a compound of Formula (I), preferably T is attached to the carbon at the 3-position of a pyridinium ring of $R^1$ and $R^2$. In other preferred embodiments, T is attached to the nitrogen of a pyridinium ring of $R^2$ and a carbon at the 3-position of a pyridinium ring of $R^1$. Preferably, T is an alkyl group or a —C≡C-alkyl-C≡C-group; more preferably, T is selected from —(CH$_2$)$_{12}$— or —C≡C—(CH$_2$)$_6$—C≡C—.

In a compound of Formula (I), preferably $X^{1\ominus}$ and $X^{2\ominus}$ are halogens. More preferably, $X^{1\ominus}$ and $X^{2\ominus}$ are bromide or iodide.

In another embodiment, the compound of Formula (I) is defined wherein $R^1$ and $R^2$ are 1,3-substituted pyridinium rings, Q is —(CH$_2$)$_4$—, —(CH$_2$)$_6$—, —(CH$_2$)$_8$—, —(CH$_2$)$_9$—, —(CH$_2$)$_{10}$—, —(CH$_2$)$_{11}$— or —(CH$_2$)$_{12}$—, T is —(CH$_2$)$_{12}$— or —C≡C—(CH$_2$)$_6$—C≡C—, and $X^1$ and $X^2$ are bromide or iodide.

Exemplary compounds of the present invention include:

N,N'-(1,6-hexanediyl)-3,3'-(1,9-decanediyn-1,10-diyl)-bis-pyridinium diiodide;

N,N'-(1,8-octananediyl)-3,3'-(1,9-decanediyn-1,10-diyl)-bis-pyridinium diiodide;

N,N'-(1,9-nonanediyl)-3,3'-(1,9-decanediyn-1,10-diyl)-bis-pyridinium dibromide;

N,N'-(1,10-decanediyl)-3,3'-(1,9-decanediyn-1,10-diyl)-bis-pyridinium diiodide;

N,N'-(1,11-undecanediyl)-3,3'-(1,9-decanediyn-1,10-diyl)-bis-pyridinium dibromide;

N,N'-(1,4-butanediyl)-3,3'-(1,12-dodecanediyl)-bis-pyridinium diiodide;

N,3'-(1,12-dodecanediyl)-3,N'-(1,12-dodecanediyl)-bis-pyridinium dibromide.

The compounds of the present invention may contain one or more stereocenters. The invention includes all possible diastereomers and all enantiomeric forms as well as all combinations of diasteriomers and enantiomers, including racemic mixtures. The compounds can be separated into substantially optically pure compounds.

Compounds of the present invention can be prepared, for example, from corresponding bases by reaction with an appropriate alkyl bromide.

The compounds of the invention are nicotinic acetylcholine receptor agents. Thus, they may augment or inhibit [$^3$H] nicotine binding, [$^3$H]MLA binding, evoke or inhibit neurotransmitter release, and/or evoke or inhibit the flux of ions through the nicotinic receptor. Moreover, the compounds of the invention may act either at presynaptic sites or postsynaptic sites, for example, at a postsynaptic acetylcholine receptor containing an α7 subunit. When acting at a postsynaptic site, neurotransmitter release per se is not altered. Rather, the compounds of the invention may act by interacting with a postsynaptic acetylcholine receptor to change the membrane potential of the cell, thereby increasing or decreasing the likelihood of firing an action potential. Alternatively, interaction of a compound of the invention with a postsynaptic acetylcholine receptor may result in the alteration of one or more second messenger systems within the cell so as to decrease or increase the nicotinic cholinergic response.

In one embodiment, the present invention relates to a method for selectively modulating the function of a nicotinic acetylcholine receptor comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

In another embodiment, the present invention is directed to a method of facilitating transport of a compound of Formula (I) into the central nervous system by interaction of the compound with the blood brain barrier choline transporter. Compounds of Formula (I) have high affinity for blood brain barrier choline transporters and have the potential to be actively transported into the CNS by this transporter. Choline transport at the blood brain barrier is a sodium-independent, carrier-mediated, and saturable process. The choline transporter binding site contains an anionic binding area that binds positively charged quaternary ammonium groups. Recent reports have shown that this transporter is efficacious in delivering quaternary ammonium analogs to the CNS. The quaternary ammonium structural characteristic of the compounds of Formula (I) provides a unique synergistic combination of nicotinic receptor interaction and affinity for the blood brain barrier choline transporter to maximize transport into the central nervous system.

In another embodiment, the present invention is directed to a method for preventing and/or treating a central nervous system associated disorder comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

Central nervous system disorders which may be treated according to the method of the present invention include Alzheimer's disease, dementia, cognitive dysfunctions (including disorders of attention, focus and concentration), attention deficit disorders, affective disorders, extrapyramidal motor function disorders, Parkinson's disease, progressive supramolecular palsy, Huntington's disease, Gilles de la Tourette syndrome, tardive dyskinesia, neuroendocrine disorders, dysregulation of food intake, disorders of nociception, pain, mood and emotional disorders, depression, panic anxiety, psychosis, schizophrenia, or epilepsy.

In yet another embodiment, the present invention is directed to a method for preventing and/or treating substance use and/or abuse comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

The conditions of substance use and/or abuse treated according to the method of the present invention include nicotine abuse (including use in smoking cessation therapy), nicotine intoxication, amphetamine abuse, methamphetamine abuse, MDMA (methylenedioxymethamphetamine) abuse, methylphenidate abuse, cocaine abuse, or alcohol abuse.

In another embodiment, the present invention is directed to a method for preventing and/or treating gastrointestinal tract disorders comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue, or may increase or prolong the release of a neurotransmitter from a peripheral nervous system tissue, or may act directly on a gastrointestinal tract tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue, or may decrease the extent or duration of the release of a neurotransmitter from a peripheral nervous system tissue, or may act directly on a gastrointestinal tract tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

Gastrointestinal disorders which may be treated according to the method of the present invention include irritable bowel syndrome, colitis, diarrhea, constipation, gastric acid secretion or ulcers.

In yet another embodiment, the present invention is directed to a method for preventing and/or treating inflammatory tract disorders comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue, or may increase or prolong the release of a neurotransmitter from a peripheral nervous system tissue, or may act directly on a non-nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue, or may decrease the extent or duration of the release of a neurotransmitter from a peripheral nervous system tissue, or may act directly on a non-nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

Inflammatory disorders which may be treated according to the method of the present invention include adult respiratory distress syndrome, allergy, anemia, ankylosing spondylitis, asthma, atherosclerosis, bacterial infections, benign prostatic hyperplasia, cholecystitis, ulcerative colitis, Crohn's disease, diabetes mellitus, emphysema, gastritis, glomerulonephritis, hypereosinophilia, irritable bowel syndrome, multiple sclerosis, osteoarthritis, pancreatitis, polymyositis, psoriasis and rheumatoid arthritis.

The compounds of the present invention can be delivered directly or in pharmaceutical compositions along with suitable carriers or excipients, as is well known in the art. For example, a pharmaceutical composition of the invention may include a conventional additive, such as a stabilizer, buffer, salt, preservative, filler, flavor enancer and the like, as known to those skilled in the art. Exemplary buffers include phosphates, carbonates, citrates and the like. Exemplary preservatives include EDTA, EGTA, BHA, BHT and the like.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences.

Suitable routes of administration may, for example, include oral, rectal, transmucosal, transdermal, topical, nasal, or intestinal administration and parenteral delivery, including intramuscular, subcutaneous, intramedullary injections, as well as intrathecal, direct intraventricular, intravenous, intraperitoneal, intranasal, or intraocular injections. In addition, the agent or composition thereof may be administered sublingually or via a spray, including a sublingual tablet or a sublingual spray. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention, the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Also, wetting agents such as sodium dodecyl sulfate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for stabilization may be employed.

For any composition used in the present methods of treatment, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein, and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

Example 1

Preparation of Compound 1,10-bis-[(pyridin-3-yl)]-1,9-decadiyne

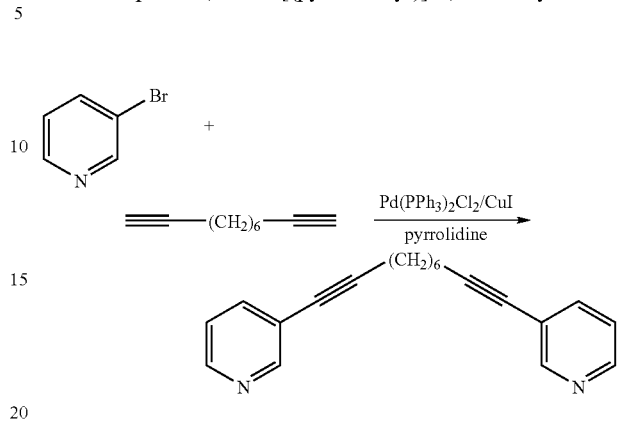

1,9-Decanediyne (2.8 g, 20.9 mmol) and 3-bromopyridine (50 mmol) were mixed in pyrrolidine followed by the addition of $Pd(PPh_3)_2Cl_2$ (50 mg) and CuI (50 mg). The mixture was heated to 60-70° C. for 2 h. The solvent was removed in vacuum and the residue was subjected chromatography. Hexane and ethyl acetate 10:1 elute out 3-bromopyridine and 2:1 hexane and ethyl acetate elute out the product (5.1 g, 85% yield) as oil. HNMR (300 MHz, $D_2O$) 8.59 (d, J=1.5 Hz, 2H), 8.43 (dd, J=1.8 Hz, J=5.1 Hz, 2H), 7.62 (dt, J=1.8 Hz, J=7.8 Hz, 2H), 7.15 (ddd, J=0.9 Hz, J=4.8 Hz, J=7.8 Hz, 2H), 2.40 (t, J=6.9 Hz, 4H), 1.59-1.63 (m, 4H), 1.46-1.49 (m, 4H).

Example 2

Preparation of Compound N,N'-(1,6-hexanediyl)-3,3'-(1,9-decanediyn-1,10-diyl)-bis-pyridinium diiodide

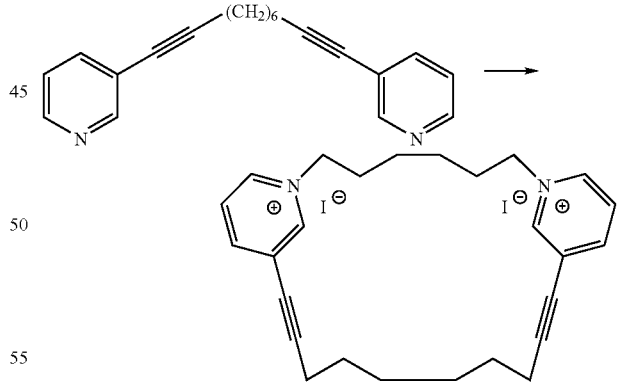

3,3'-(1,9-Decanediyn-1,10-diyl)-bis-pyridine (1 mmol) and an equivalent of 1,6-diiodohexane were mixed in acetonitrile (1000 mL). The mixture was refluxed for 7 days. The solvent was removed in vacuum after cooling and the resulting residue was taken up in water and partitioned between ethyl ether and water. The aqueous layer was extracted extensively with ethyl ether remove the starting materials. Most of the water was removed and the residue was transferred into methanol. Methanol was removed and the product was dried under vacuum to afford the bis-pyridinium cyclophane (30% yield). HNMR (300 MHz, D₂O) 8.76 (s, 2H), 8.56 (d, J=6.0 Hz, 2H), 8.29 (d, J=8.4 Hz, 2H), 7.81 (dd, J=6.3 Hz, 8.1 Hz, 2H), 4.40 (t, J=7.5 Hz, 4H), 2.39 (t, J=6.3 Hz, 4H), 1.85-1.84 (m, 4H), 1.49-1.52 (m, 4H), 1.38-1.42 (m, 4H), 1.18-1.22 (m, 4H). CNMR, 146.97, 146.26, 142.61, 128.00, 125.71, 101.43, 73.93, 61.99, 29.94, 27.84, 27.49, 24.43, 18.90.

Example 3

Preparation of Compound N,N'-(1,8-octanediyl)-3,3'-(1,9-decanediyn-1,10-diyl)-bis-pyridinium diiodide

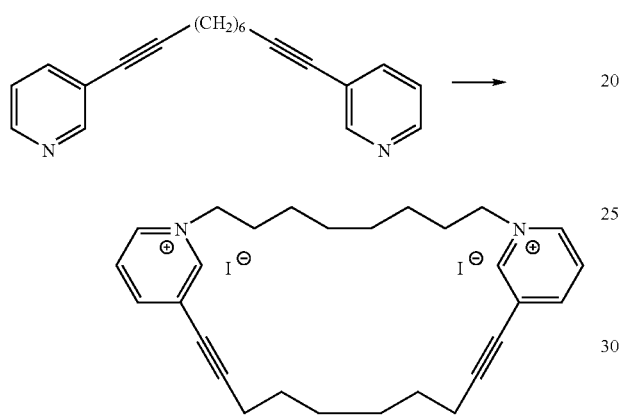

3,3'-(1,9-Decanediyn-1,10-diyl)-bis-pyridine (1 mmol) and an equivalent of 1,8-diiodooctane were mixed in acetonitrile (1000 mL). The mixture was refluxed for 7 days. The solvent was removed in vacuo after cooling and the resulting residue was taken up in water and partitioned between diethyl ether and water. The aqueous layer was extracted extensively with diethyl ether to remove the starting materials. Most of the water was removed and the residue was transferred into methanol. Methanol was removed and dried under vacuum to afford the bis-pyridinium cyclophane (35% yield). HNMR (300 MHz, D₂O) 10.30 (s, 2H), 9.37 (d, J=5.7, 2H), 8.19 (d, J=8.1, 2H), 7.94 (dd, J=8.1, J=6.0, 2H), 4.95 (t, J=8.4, 4H), 2.49 (t, J=6.6, 4H), 2.14-2.22 (m, 4H), 1.75-1.85 (m, 4H), 1.61-1.68 (m, 8H), 1.54-1.58 (br, 8H), 1.49-4.58 (br, 4H).

Example 4

Preparation of Compound N,N'-(1,9-nonanediyl)-3,3'-(1,9-decanediyn-1,10-diyl)-bis-pyridinium dibromide

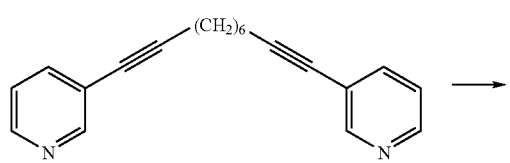

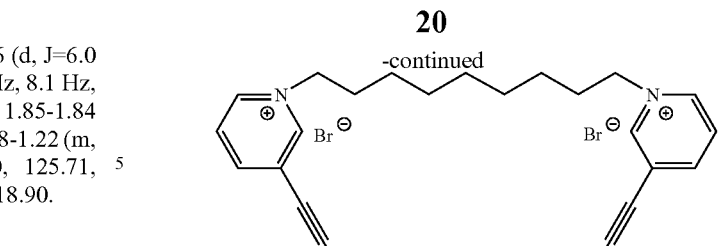

3,3'-(1,9-Decanediyn-1,10-diyl)-bis-pyridine (1 mmol) and an equivalent of 1,9-dibromononane were mixed in acetonitrile (1000 mL). The mixture was refluxed for 7 days. The solvent was removed in vacuo after cooling and the resulting residue was taken up in water and partitioned between diethyl ether and water. The aqueous layer was extracted extensively with diethyl ether remove the starting materials. Most of the water was removed and the residue was transferred into methanol. Methanol was removed and the product was dried under vacuum to afford the bis-pyridinium cyclophane (38% yield) HNMR (300 MHz, D₂O) 10.39 (s, 2H), 9.52 (d, J=5.7, 2H), 8.18 (d, J=7.5, 8.00 (m, 2H), 5.06 (t, J=7.2, 4H), 2.49 (t, J=6.3, 4H), 2.08-2.18 (br, 4H), 1.60-1.80 (br, 12H), 1.42-1.56 (br, 8H), 1.37-1.40 (br, 2H).

Example 5

Preparation of Compound N,N'-(1,10-decanediyl)-3,3'-(1,9-decanediyn-1,10-diyl)-bis-pyridinium diiodide

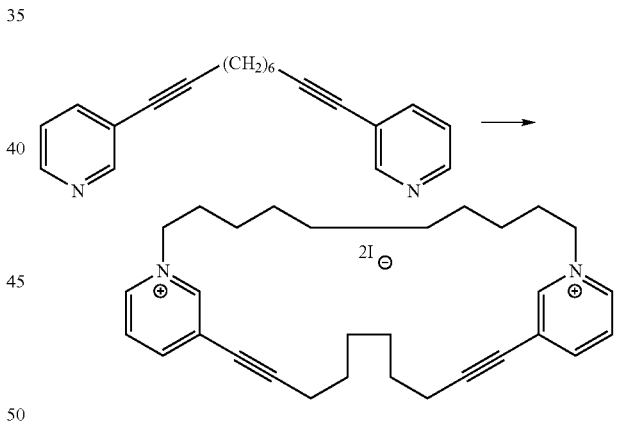

3,3'-(1,9-Decanediyn-1,10-diyl)-bis-pyridine (1 mmol) and an equivalent of 1,10-diiododecane were mixed in acetonitrile (1000 mL). The mixture was refluxed for 7 days. The solvent was removed in vacuo after cooling and the resulting residue was taken up in water and partitioned between diethyl ether and water. The aqueous layer was extracted extensively with diethyl ether remove the starting materials. Most of the water was removed and the residue was transferred into methanol. Methanol was removed and the product was dried under vacuum to afford the bis-pyridinium cyclophane (40% yield). HNMR (300 MHz, D₂O), 10.11 (s, 2H), 9.37 (d, J=6.3, 2H), 8.22 (dt, J=7.8, J=1.2, 2H), 8.03 (dd, J=6.3, J=7.8, 2H), 4.99 (t, J=8.1, 4H), 2.49 (t, J=6.6, 4H), 2.15-2.17 (m, 4H), 1.38-1.75 (m, 24H). CNMR, 147.73, 145.88, 142.71, 128.04, 126.46, 102.54, 74.29, 61.82, 32.44, 28.71, 27.90, 27.83, 27.40, 25.81, 20.21.

Example 6

Preparation of Compound N,N'-(1,11-undecanediyl)-3,3'-(1,9-decanediyn-1,10-diyl)-bis-pyridinium dibromide

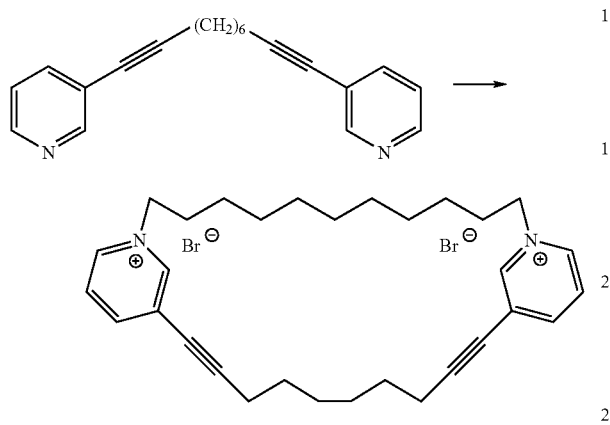

3,3'-(1,9-Decanediyn-1,10-diyl)-bis-pyridine (1 mmol) and an equivalent of 1,11-dibromoundecane were mixed in acetonitrile (1000 mL). The mixture was refluxed for 7 days. The solvent was removed in vacuo after cooling and the resulting residue was taken up in water and partitioned between diethyl ether and water. The aqueous layer was extracted extensively with diethyl ether remove the starting materials. Most of the water was removed and the residue was transferred into methanol. Methanol was removed and the product was dried under vacuum to afford the bis-pyridinium cyclophane (42% yield). HNMR (300 MHz, D$_2$O), 9.92 (s, 2H), 9.48 (d, J=7.8, 2H), 8.22 (d, J=8.1, 2H), 8.05 (m, 2H), 5.08 (br, 4H), 2.49 (t, J=6.3, 4H), 2.05-2.15 (br, 4H), 1.70-1.82 (br, 12H), 1.55-1.65 (br, 4H), 1.45-1.55 (br, 4H), 1.30-1.45 (8H).

Example 7

Preparation of Compound 1,12-bis-(pyridin-3-yl)-dodecane

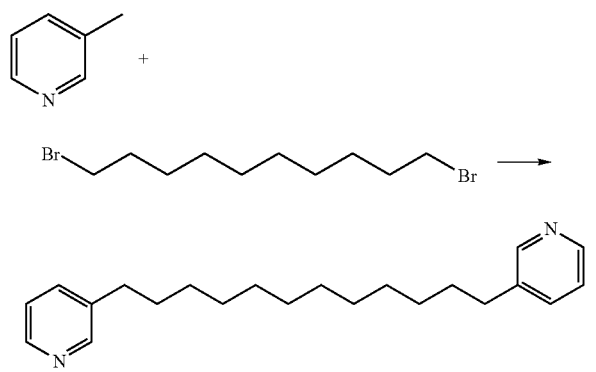

LDA (2M) (20.40 mL, 40.80 mmol) was added drop-wise to a solution of 3-picoline (3.80 g, 40.80 mmol) in THF (60 mL) at −78° C. The mixture was stirred for 30 min and then 1,10-dibromodecane (6.43 g, 16.32 mmol) in THF (10 mL) was added drop-wise. The resulting mixture was warmed to room temperature and stirred for 4 hrs. Fifty percent saturated NH$_4$Cl was added to the reaction mixture. The aqueous phase was extracted with ethylacetate (2×40 mL), and the combined organic liquors were washed with 50% saturated brine (3×40 mL) and saturated brine (40 mL), dried over anhydrous Na$_2$SO$_4$, and concentrated under reduced pressure. The crude product was purified by column chromatography (hexanes: ethylacetate 2:1 to 1:1) to afford 3.98 g of the title compound. Yield: 75%. $^1$H NMR (300 MHz, CDCl$_3$) δ 1.17-1.40 (m, 16H), 1.53-1.68 (m, 4H), 2.60 (t, J=7.5 Hz, 4H), 7.20 (dd, J=7.8, 1.8 Hz, 2H), 7.48 (dt, J=7.8, 1.8 Hz, 2H), 8.43 (d, J=5.1 Hz, 2H), 8.44 (s, 2H) ppm; $^{13}$C NMR (75 MHz, CDCl$_3$) δ 29.4, 29.7, 29.8, 29.9, 31.4, 33.3, 123.3, 135.8, 138.4, 147.2, 150.0 ppm.

Example 8

Preparation of Compound N,N'-(1,4-butanediyl)-3,3'-(1,12-dodecanediyl)-bis-pyridinium diiodide

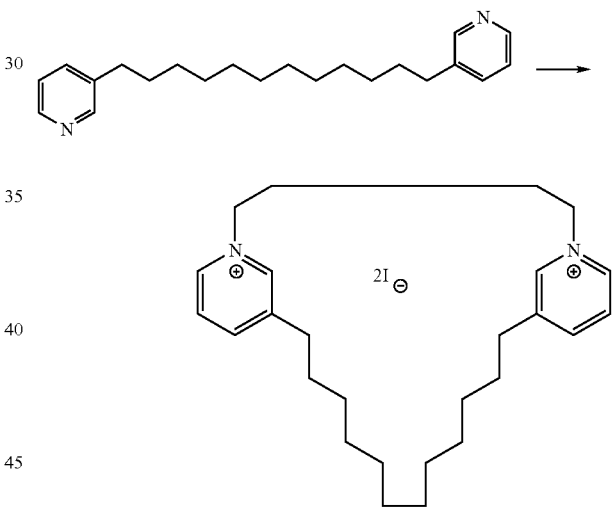

3,3'-(Dodecan-1,12-diyl)-bis-pyridine (1 mmol) and an equivalent of 1,4-diiodobutane were mixed in 4-methyl-2-pentanol (265 mL). The mixture was refluxed for 28 days. The solvent was removed in vacuo after cooling and the resulting residue was taken up in methylene chloride and water (50 mL, 1:1). The methylene chloride layer containing the mono-quaternary ammonium product was removed and the remaining aqueous layer further extracted with methylene chloride (3×25 mL). The water layer containing the bis-pyridinium product was evaporated under reduced pressure to low volume (0.5 mL) and transferred into methanol (5 mL). The methanol was removed and the product was dried under vacuum to afford the bis-pyridinium cyclophane (35% yield). $^1$H NMR (300 MHz, CD$_3$OD) δ 1.21-1.46 (m, 16H), 1.72 (m, 4H), 2.18 (m, 4H), 2.56 (s, 6H), 2.81 (t, J=7.5 Hz, 4H), 4.68 (m, 4H), 8.28 (s, 2H), 8.79 (s, 2H), 8.83 (s, 2H) ppm; $^{13}$C NMR (75 MHz, CD$_3$OD) δ 18.8, 28.8, 28.9, 29.4, 29.6, 30.8, 33.5, 61.7, 140.9, 142.3, 143.3, 144.9, 147.6 ppm.

Example 9

Preparation of Compound
12-(pyridin-3-yl)-1-bromododecane

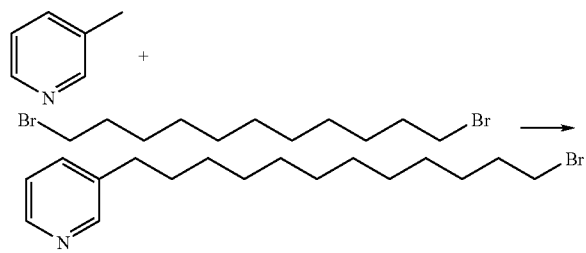

LDA (2 M) (10.5 mL, 21.22 mmol) was added drop-wise to a solution of 3-picoline (2.17 g, 23.34 mmol) in THF (60 mL) at −78° C. The mixture was stirred for 30 min and then 1,11-dibromoundecane (10 g, 31.83 mmol) was added in one portion. The resulting mixture was warmed to 0° C. and stirred for 4 hrs. Fifty percent saturated $NH_4Cl$ was added to the reaction mixture. The aqueous phase was extracted with ethylacetate (2×40 mL), and the combined organic liquors were washed with 50% saturated brine (3×40 mL) and saturated brine (40 mL), dried over anhydrous $Na_2SO_4$, and concentrated under reduced pressure. The crude product was purified by column chromatography (hexanes:ethylacetate 4:1) to afford 4.47 g 12-(pyridin-3-yl)-1-bromododecane. Yield: 59%.

Example 10

Preparation of Compound N,3'-(1,12-dodecanediyl)-3,N'-(1,12-dodecanediyl)-bis-pyridinium dibromide

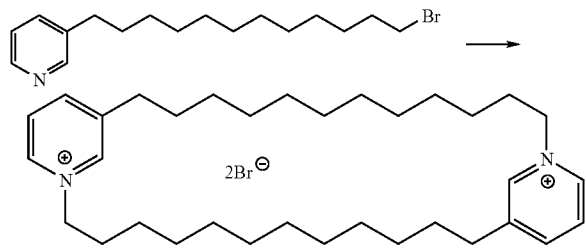

12-(Pyridin-3-yl)-1-bromododecane was dissolved in acetonitrile (250 mL). The mixture was refluxed for 24 hours. The solvent was removed in vacuo after cooling and the resulting residue was taken up by water and diethyl ether (50 mL, 1:1). The diethyl ether layer containing the starting material was removed and the remaining aqueous layer further extracted with diethyl ether (3×25 mL). The water layer containing the bis-pyridinium product was evaporated under reduced pressure to low volume (0.5 mL) and transferred into methanol (5 mL). The methanol was removed and the product was dried under vacuum to afford the bis-pyridinium cyclophane (25% yield). $^1H$ NMR (300 MHz, DMSO-$d_6$) δ 1.15-1.39 (m, 32H), 1.63 (m, 4H), 1.90 (m, 4H), 2.78 (t, J=7.8 Hz, 4H), 4.57 (t, J=7.2 Hz, 4H), 8.08 (dd, J=8.1, 6.0 Hz, 2H), 8.48 (d, J=8.1 Hz, 2H), 8.98 (d, J=6.0 Hz, 2H), 9.10 (s, 2H) ppm; $^{13}C$ NMR (75 MHz, $CD_3OD$) δ 25.5, 28.5, 28.8, 28.9, 29.0, 29.9, 30.7, 31.7, 60.5, 127.4, 142.1, 142.8, 143.8, 144.9 ppm.

Example 11

Inhibition of [$^3H$]nicotine and [$^3H$]Methyllycaconitine Binding Assays

Whole brain, excluding cortex and cerebellum, was homogenized in 20 vol of ice-cold buffer, containing (in mM): 2 HEPES, 11.8 NaCl, 0.48 KCl, 0.25 $CaCl_2$ and 0.12 $MgSO_4$, pH 7.5. Homogenate was centrifuged (25,000 g, 15 min, 4° C.). Pellets were resuspended in 20 vol buffer and incubated at 37° C., for 10 min, cooled to 4° C. and centrifuged (25,000 g, 15 min, 4° C.). Pellets were resuspended and centrifuged using the same conditions. Final pellets were stored in assay buffer, containing (in mM): 20 HEPES, 118 NaCl, 4.8 KCl, 2.5 $CaCl_2$, and 1.2 $MgSO_4$, pH 7.5 at −70° C. Upon use, final pellets were resuspended in ~20 vol assay buffer. Samples (250 μl) contained 100-140 μg of membrane protein, 3 nM [$^3H$]nicotine or 3 nM [$^3H$]methyllycaconitine (MLA), and bis-quaternary ammonium cyclophane analog (100 nM) in assay buffer containing 50 mM Tris. Control was in the absence of analog. In [$^3H$]nicotine and [$^3H$]methyllycaconitine binding assays, nonspecific binding was determined in the presence of 10 μM cytisine and 10 μM nicotine, respectively. Incubations proceeded for 60 min at room temperature using 96-well plates and were terminated by harvesting on Unifilter-96 GF/B filter plates presoaked in 0.5% polyethylenimine, using a Packard FilterMate harvester. After washing 5 times with 350 μl ice-cold assay buffer, filter plates were dried (60 min, 4° C.), bottom-sealed, and filled with Packard's MicroScint 20 cocktail (40 μl/well). After 60 min, filter plates were top-sealed, and radioactivity determined using a Packard TopCount. Protein concentrations were determined using the Bradford dye-binding procedure bovine serum albumin as the standard. The results are summarized in Table 1.

Example 12

Inhibition of Nicotine-evoked [$^3H$]Neurotransmitter Release Assay

Rat striatal slices (500 μm thickness, 6-8 mg wet weight) were incubated for 30 minutes in Krebs buffer (118 mM NaCl, 4.7 mM KCl, 1.2 mM $MgCl_2$, 1.0 mM $NaH_2PO_4$, 1.3 mM $CaCl_2$, 11.1 mM glucose, 25 mM $NaHCO_3$, 0.11 mM L-ascorbic acid, and 0.004 mM disodium EDTA; pH 7.4, and saturated with 95% $O_2$/5% $CO_2$) in a metabolic shaker at 34° C. Slices were rinsed with 15 mL of fresh buffer and incubated for an additional 30 minutes in fresh buffer containing 0.1 μM [$^3H$]dopamine (DA; 6 slices/3 mL). Subsequently, slices were rinsed with 15 mL of fresh buffer and transferred to a glass superfusion chamber. Slices were superfused (1.0 mL/min) for 60 minutes with Krebs buffer containing nomifensine (10 μM) and pargyline (10 μM) and maintained at 34° C., pH 7.4, with continual aeration (95% $O_2$/5% $CO_2$). Two five minute samples (5 mL each) were collected to determine basal outflow of [$^3H$]DA. The bis-quaternary ammonium cyclophane analogs were added to the superfusion buffer after the collection of the second sample and remained in the buffer until 12 consecutive five minute samples were collected. Subsequently, S-(−)-nicotine (10 μM) was added to the buffer and an additional 12 consecutive five minute samples were collected. At the end of the experiment, each slice was solubilized and the [$^3$H] content of the tissue determined.

Radioactivity in the superfusate and tissue samples was determined by liquid scintillation spectroscopy. Fractional release for tritium collected in each sample was divided by the total tritium present in the tissue at the time of sample collection and was expressed as a percentage of total tritium. Basal [$^3$H]outflow was calculated from the average of the tritium collected in the two five minute samples just before addition of the quaternary ammonium analog. The sum of the increase in collected tritium resulting from either exposure to the test compound or exposure to S-(−)-nicotine in the absence and presence of the test compound equaled total [$^3$H]overflow. [$^3$H]Overflow was calculated by subtracting the [$^3$H]outflow during an equivalent period of prestimulation from the values in samples collected during and after drug exposure. Inasmuch as the radiolabelled compounds were not separated and identified, the tritium collected in superfusate is referred to as either [$^3$H]outflow or [$^3$H]overflow, rather than as [$^3$H]DA. [$^3$H]Overflow primarily represents [$^3$H]DA in the presence of nomifensine and pargyline in the superfusion buffer.

The bis-quaternary ammonium cyclophane analogs were evaluated for their ability to evoke [$^3$H]DA release from rat striatal slices. In addition, the classical competitive nicotinic antagonist DHβE was also examined in this assay for comparison. None of the compounds examined had any significant [$^3$H]DA releasing properties in this assay in the concentration range tested.

The bis-quaternary ammonium cyclophane analogs were also evaluated for their ability to inhibit nicotine evoked [$^3$H] DA release. In these experiments, the striatal slices were superfused for 60 minutes with 100 nM concentration of the bis-quaternary ammonium cyclophane analogs prior to nicotine (10 μM) exposure. Antagonist activity was evaluated by comparing the nicotine evoked [$^3$H]overflow in the absence and presence of the analogs. The relative order of potency of the bis-quaternary ammonium cyclophane analogs for inhibition of nicotine-evoked [$^3$H]DA release from rat striatal slices is illustrated in Table 1.

Table 1. Bis-Quaternary Ammonium Cyclophane Compounds: Affinity for the BBB Choline Transporter, Inhibition of [$^3$H]Nicotine and [$^3$H]Methyllycaconitine (MLA) Binding to Rat Striatal Nicotinic Receptors and Inhibition of Nicotine-evoked [$^3$H]Dopamine Release from Superfused Rat Striatal Slices

| COMPOUND | Affinity for the BBB choline transporter Ki (μM) | Inhibition of [$^3$H]Nicotine binding[a] | Inhibition of [$^3$H]MLA Binding[b] | Inhibition of Nicotine-evoked [$^3$H]DA release[c] |
|---|---|---|---|---|
| Example 2 | 33.6 | 7% | 2% | ND |
| Example 3 | ND | 9% | 0% | ND |
| Example 4 | 1.4 | 0% | 3% | ND |

| COMPOUND | Affinity for the BBB choline transporter Ki (μM) | Inhibition of [³H]Nicotine binding[a] | Inhibition of [³H]MLA Binding[b] | Inhibition of Nicotine-evoked [³H]DA release[c] |
|---|---|---|---|---|
| Example 5 | 0.8 | 0.55 (Ki, μM) | 4.64 (Ki, μM) | 19% |
| Example 6 | 15.2 | 11% | 3% | ND |
| Example 8 | ND | 14 ± 2.6% | 3.0 ± 3.0% | 23% |
| Example 10 | ND[d] | 2% | 0% | 20% |

[a] Data are % inhibition at 100 nM concentration of the bis-quaternary ammonium cyclophane analogs for at least 1-3 independent experiments; with the exception of when a Ki value in μM is provided, in which case a full concentration effect was evaluated. Specific binding in the [³H]nicotine binding assay is calculated as the difference between the total binding of 3 nM [³H]nicotine and nonspecific binding in the presence of 10 μM cold cytisine.
[b] Specific binding for the [³H]MLA binding assay is calculated as the difference between the total binding of 2.5 nM [³H]MLA to the receptors alone and its nonspecific binding in the presence of 1 μM cold nicotine.
[c] Analog-induced inhibition of nicotine-evoked [³H]DA release is calculated as a percent of that in the absence of bis-quaternary ammonium cyclophane analog.
[d] ND indicates not determined.

It will be appreciated that, although specific embodiments of the invention have been described herein for purposes of illustration, various modifications may be made without departing from the spirit and scope of the invention. All such modifications and variations are intended to be included herein within the scope of this disclosure and the present invention and protected by the following claims.

We claim:

1. A compound of Formula (I)

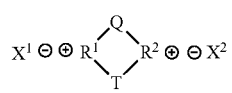

(I)

wherein
$X^{1\ominus}$ and $X^{2\ominus}$ are each independently an organic or inorganic anion;
Q and T are each independently attached to $R^1$ and $R^2$;
Q is alkyl;
T is alkynyl;
$R^1$ and $R^2$ are each six membered rings as shown in formula (IIA);

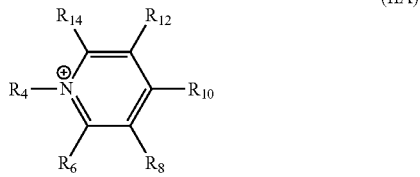

(IIA)

$R^8$ or $R^{12}$ is replaced by one attachment to T in $R^1$ and $R^2$;
$R^4$ is replaced by one attachment to Q in $R^1$ and $R^2$;
$R^6$, $R^8$, $R^{10}$, $R^{12}$, and $R^{14}$, when present, are each independently selected from the group consisting of hydrogen, lower alkyl, halo, cyano, nitro, trifluoromethyl, hydroxymethyl, hydroxyethyl and hydroxypropyl.

2. The compound of claim 1, wherein Q is —$(CH_2)_4$—, —$(CH_2)_6$—, —$(CH_2)_8$—, —$(CH_2)_9$—, —$(CH_2)_{10}$—, —$(CH_2)_{11}$— or —$(CH_2)_{12}$—; and T is —C≡C—$(CH_2)_6$—C≡C—.

3. The compound of claim 2, wherein
$X^{1\ominus}$ and $X^{2\ominus}$ are bromide or iodide.

4. The compound of claim 1 selected from the group consisting of:
N,N'-(1,6-hexanediyl)-3,3'-(1,9-decanediyn-1,10-diyl)-bis-pyridinium diiodide;
N,N'-(1,8-octananediyl)-3,3'-(1,9-decanediyn-1,10-diyl)-bis-pyridinium diiodide;
N,N'-(1,9-nonanediyl)-3,3'-(1,9-decanediyn-1,10-diyl)-bis-pyridinium dibromide;
N,N'-(1,10-decanediyl)-3,3'-(1,9-decanediyn-1,10-diyl)-bis-pyridinium diiodide; and
N,N'-(1,11'-undecanediyl)-3,3'-(1,9-decanediyn-1,10-diyl)-bis-pyridinium dibromide.

5. A composition comprising a pharmaceutically acceptable carrier and a compound of claim 1.

6. A composition comprising a pharmaceutically acceptable carrier and a compound of claim 2.

7. A composition comprising a pharmaceutically acceptable carrier and a compound of claim 3.

8. A composition comprising a pharmaceutically acceptable carrier and a compound of claim 4.

9. N,N'-(1,4-butanediyl)-3,3'-(1,12-dodecanediyl)-bis-pyridinium diiodide.

* * * * *